(12) United States Patent
Zou

(10) Patent No.: US 10,286,166 B2
(45) Date of Patent: May 14, 2019

(54) PRESSURE INDICATOR

(71) Applicant: Dewei Zou, Tianjin (CN)

(72) Inventor: Dewei Zou, Tianjin (CN)

( * ) Notice: Subject to any disclaimer, the term of this patent is extended or adjusted under 35 U.S.C. 154(b) by 788 days.

(21) Appl. No.: 14/924,692

(22) Filed: Oct. 27, 2015

(65) Prior Publication Data

US 2016/0045688 A1 Feb. 18, 2016

Related U.S. Application Data

(63) Continuation-in-part of application No. PCT/CN2014/077546, filed on May 15, 2014.

(30) Foreign Application Priority Data

Nov. 14, 2013 (CN) .......................... 2013 1 0575100
Nov. 14, 2013 (CN) ..................... 2013 2 0727634 U

(51) Int. Cl.
| | |
|---|---|
| *A61M 16/00* | (2006.01) |
| *G01L 13/02* | (2006.01) |
| *G01L 19/10* | (2006.01) |
| *A61M 16/04* | (2006.01) |
| *A61M 25/10* | (2013.01) |
| *A61M 16/08* | (2006.01) |
| *A61M 16/20* | (2006.01) |

(52) U.S. Cl.
CPC ...... *A61M 16/0003* (2014.02); *A61M 16/044* (2013.01); *A61M 16/0816* (2013.01); *A61M 16/208* (2013.01); *A61M 25/10187* (2013.11); *G01L 13/02* (2013.01); *G01L 19/10* (2013.01); *A61M 2016/0027* (2013.01); *A61M 2205/3348* (2013.01)

(58) Field of Classification Search
USPC .......................................................... 73/715
See application file for complete search history.

(56) References Cited

U.S. PATENT DOCUMENTS

| | | | | |
|---|---|---|---|---|
| 5,025,244 A | * | 6/1991 | Huang | ................ B60C 23/0408 116/34 R |
| 5,687,672 A | * | 11/1997 | Gabriel | ............... B60C 23/0496 116/272 |
| 5,781,104 A | * | 7/1998 | Huang | ................ B60C 23/0408 310/318 |

(Continued)

*Primary Examiner* — Paul M. West
*Assistant Examiner* — Mark A Shabman
(74) *Attorney, Agent, or Firm* — Matthias Scholl P.C.; Matthias Scholl

(57) ABSTRACT

A pressure indicator, including: a check valve; an upper cover; an intermediate member; an elastic pressure-sensing diaphragm; a transmission indication rod; and a lower cover. The check valve is disposed in the upper cover, and the inner wall of the upper cover and the check valve are assembled to form an upper opening. The opening of an air channel which communicates with the air is disposed inside the circular groove. The positioning bulge of the upper cover is connected to the positioning groove of the intermediate member. The lower port of the intermediate member is bonded with the circumferential flange of the elastic pressure-sensing diaphragm. The lower surface of the elastic pressure-sensing diaphragm is provided with a groove configured to coordinate with the support end of the transmission indication rod. The connection rod is connected to the top and bottom of the support end.

4 Claims, 4 Drawing Sheets

(56) References Cited

U.S. PATENT DOCUMENTS

| | | | | |
|---|---|---|---|---|
| 6,525,655 B2* | 2/2003 | Huang | ................... | B60C 23/04 |
| | | | | 116/34 R |
| 6,911,903 B2* | 6/2005 | Gladstone | ........... | B60C 23/0496 |
| | | | | 116/34 R |
| 2008/0190189 A1* | 8/2008 | Milanovich | ......... | B60C 23/0496 |
| | | | | 73/146.8 |

* cited by examiner

PRESSURE INDICATOR

CROSS-REFERENCE TO RELATED APPLICATIONS

This application is a continuation-in-part of International Patent Application No. PCT/CN2014/077546 with an international filing date of May 15, 2014, designating the United States, now pending, and further claims priority benefits to Chinese Patent Application No. 201320727634.8 filed Nov. 14, 2013 and to Chinese Patent Application No. 201310575100.2 filed Nov. 14, 2013. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18$^{th}$ Floor, Cambridge, Mass. 02142.

BACKGROUND OF THE INVENTION

Field of the Invention

This invention relates to a pressure indicator used to measure and indicate the pressure in a laryngeal mask, tracheal intubation or catheter.

Description of the Related Art

Typical pressure indicators have narrow indication range, limited adaptability, low accuracy, and thus cannot meet the present requirements.

SUMMARY OF THE INVENTION

In view of the above-described problems, it is one objective of the invention to provide a pressure indicator which features a compact structure, accurate indication and wide application.

To achieve the above objective, in accordance with one embodiment of the invention, there is provided a pressure indicator, comprising: a check valve; an upper cover, the upper cover comprising an inner wall, a circular groove, and a positioning bulge; an intermediate member, the intermediate member comprising a positioning groove, a lower port; an elastic pressure-sensing diaphragm, the elastic pressure-sensing diaphragm comprising a circumferential flange, a lower surface; a transmission indication rod, the transmission indication rod comprising a support end, a connection rod, and an indication end; and a lower cover. The check valve is disposed in the upper cover, and the inner wall of the upper cover and the check valve are assembled to form an upper opening. The circular groove is disposed on a shoulder of the upper cover; an opening of an air channel which communicates with the air is disposed inside the circular groove. The positioning bulge of the upper cover is connected to the positioning groove of the intermediate member. The lower port of the intermediate member is bonded with the circumferential flange of the elastic pressure-sensing diaphragm. The lower surface of the elastic pressure-sensing diaphragm is provided with a groove configured to coordinate with the support end of the transmission indication rod. The connection rod is connected to a top and bottom of the support end, and the indication end comprises holes on two sides thereof.

In a class of this embodiment, the air channel is formed by and runs through the upper cover and the intermediate member.

In a class of this embodiment, at least one surface of the elastic pressure-sensing diaphragm is provided with at least one circular or oval circumferential reinforcing bar and at least one longitudinal reinforcing bar which diffuses from center to all round. The longitudinal reinforcing bar is between 2 and 16 in number. The longitudinal reinforcing bar and the circumferential reinforcing bar are uniformly distributed in a vertically crossing way; and a cross section of the circumferential reinforcing bar and the longitudinal reinforcing bar is designed to be waved, rectangular, triangular or other geometrical shapes.

In a class of this embodiment, the elastic pressure-sensing diaphragm is a circular chip, oval chip or chip with other geometrical shapes, with a thickness thereof of between 0.1 mm and 2.0 mm.

In a class of this embodiment, the elastic pressure-sensing diaphragm is made of rubber, silastic, thermoplastic elastomer (TPE) or other high elastic macromolecule material.

Compared with existing technologies, advantages of the pressure indicator according to embodiments of the invention are given below:

1. Wide range of pressure indication, specifically, the water column ranges from 10 cm to 100 cm.
2. High indication accuracy and high differentiability.
3. High adaptability, enabling it to be used in the monitoring and measurement of air pressure and hydraulic pressure.

In the figures, the following reference numbers are used: 1. Upper cover; 1-1. Upper opening; 1-2. Check valve; 1-3. Lower space; 1-4. Gap; 1-5. Air channel; 1-6. Circular groove; 1-7. Positioning bulge; 2. Intermediate member; 2-1. Bonding gap; 2-2. Lower port; 2-3. Positioning groove; 2-4. Airway; 2-5. Air channel; 3. Elastic pressure-sensing diaphragm; 3-1. Circumferential flange; 3-2. Upper surface; 3-3. Lower surface; 3-4. Circumferential reinforcing bar; 3-5. Longitudinal reinforcing bar; 3-6. Groove; 4. Transmission indication rod; 4-1. Support end; 4-2. Connection rod; 4-3. Hole; 4-4. Indication end; 5. Lower cover; 5-1. Upper space; 5-2. Lower space; 5-3. Lower mouth.

DETAILED DESCRIPTION OF THE EMBODIMENTS

For further illustrating the invention, experiments detailing a pressure indicator are described below. It should be noted that the following examples are intended to describe and not to limit the invention.

Figure 1:
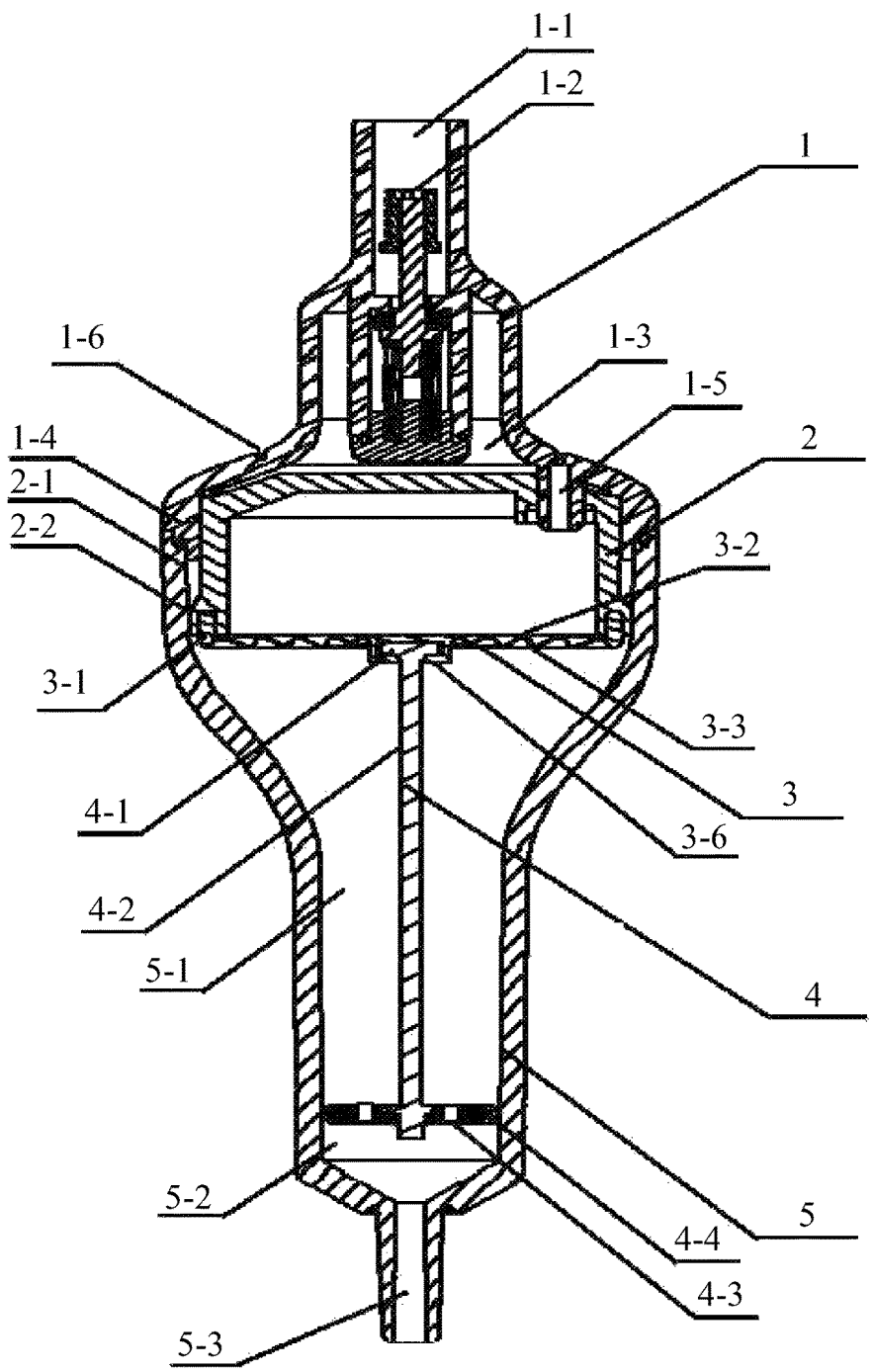
FIG. 1 is a cross-sectional view of a pressure indicator in accordance with one embodiment of the invention.
Figure 2:
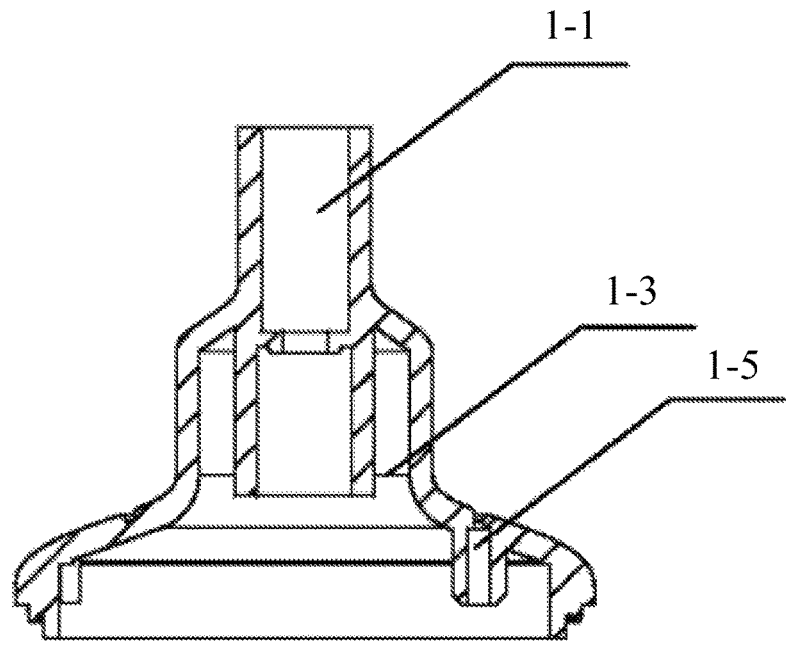
FIG. 2 is a sectional view of an upper cover of a pressure indicator in accordance with one embodiment of the invention.
Figure 3:
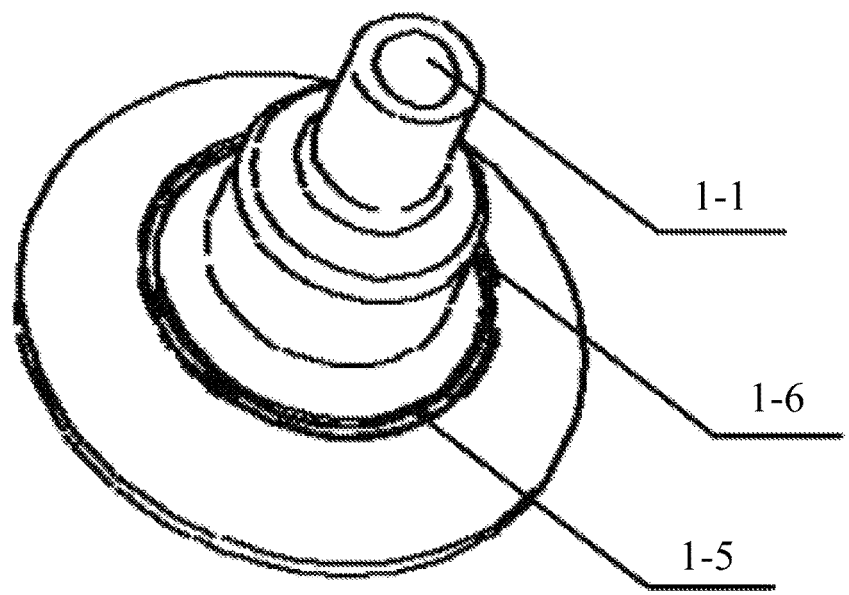
FIG. 3 is a top view of an upper cover of a pressure indicator in accordance with one embodiment of the invention.
Figure 4:
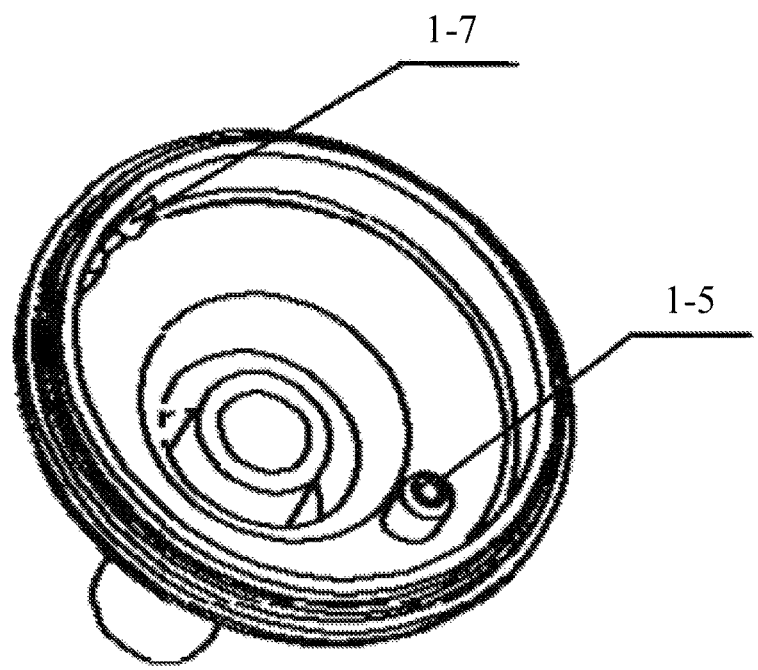
FIG. 4 is a bottom view of an upper cover of a pressure indicator in accordance with one embodiment of the invention.
Figure 5:
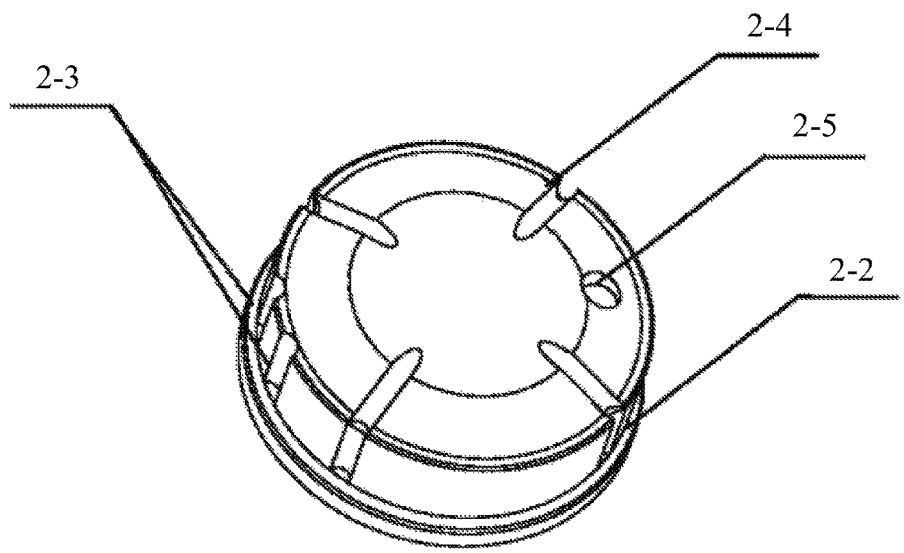
FIG. 5 is a schematic diagram of an intermediate member of a pressure indicator in accordance with one embodiment of the invention.

As shown in FIG. 1, a pressure indicator comprises: an upper cover 1, an intermediate member 2, an elastic pressure-sensing 3, a transmission indication rod 4, and a lower cover 5. As shown in FIGS. 2-4, a check valve 1-2 is disposed in the upper cover 1, and the inner wall of the upper cover and the check valve 1-2 are assembled to form the upper opening 1-1. A circular groove 1-6 is disposed on the shoulder of the upper cover. The opening of the air channel 1-5 which communicates with the air is disposed inside the circular groove 1-6. The positioning bulge 1-7 of the upper cover 1 is connected to the positioning groove 2-3 of the intermediate member 2.

The lower port 2-2 of the intermediate member 2 is bonded with the circumferential flange 3-1 of the elastic pressure-sensing diaphragm 3. A groove 3-6 which coordinates with the support end 4-1 of the transmission indication rod 4 is disposed on the lower surface 3-3 of the elastic pressure-sensing diaphragm 3, as shown in FIG. 1.

The transmission indication rod 4 comprises: support end 4-1, connection rods 4-2 respectively connected to the top and bottom of the support end 4-1, indication end 4-4 and holes 4-3 on two sides, as shown in FIG. 1.

As shown in FIG. 1, the air channel 1-5 is formed by and runs through the upper cover 1 and the intermediate member 2.

Figure 6:
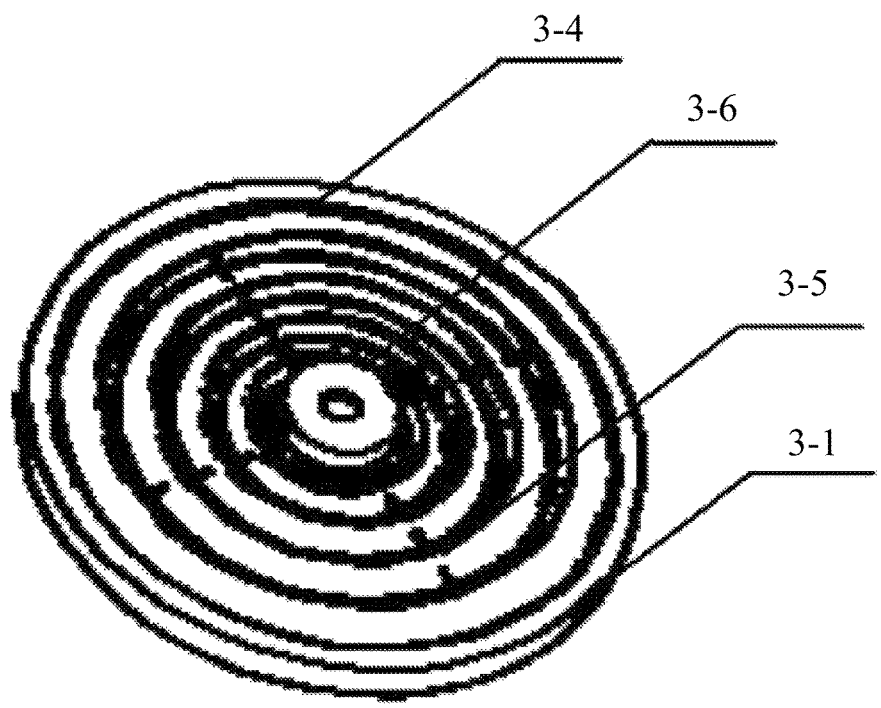
FIG. 6 is a schematic diagram of an elastic pressure-sensing diaphragm of a pressure indicator in accordance with one embodiment of the invention.
Figure 7:
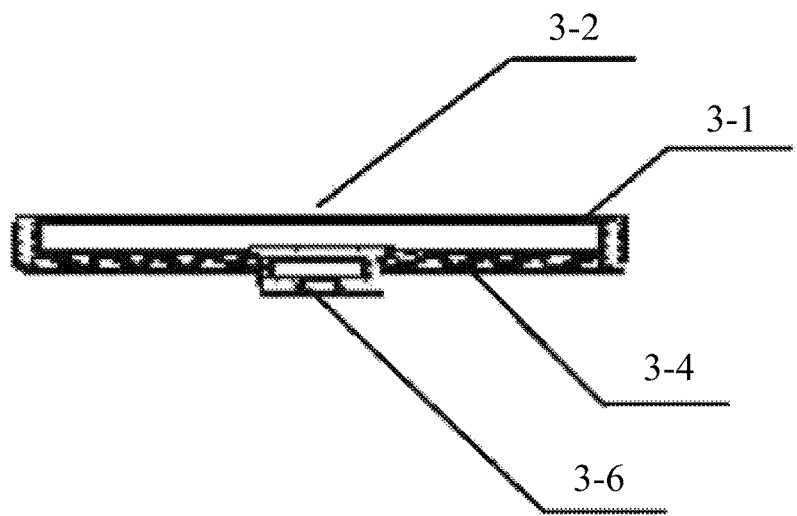
FIG. 7 is a cross-sectional view of an elastic pressure-sensing diaphragm of a pressure indicator in accordance with one embodiment of the invention.

As shown in FIGS. 6-7, at least one surface of the elastic pressure-sensing diaphragm 3 is provided with at least one circular or oval circumferential reinforcing bar 3-4 and at least one longitudinal reinforcing bar 3-5 which diffuses from center to all round. The longitudinal reinforcing bar 3-5 is between 2 and 16 in number, which is 4 in this example. The longitudinal reinforcing bar 3-5 and the circumferential reinforcing bar 3-4 are equally distributed in a vertically crossing way. The cross section of the circumferential reinforcing bar 3-4 and the longitudinal reinforcing bar 3-5 is designed to be waved, rectangular, triangular or other geometrical shapes. In this example, the cross section of the circumferential reinforcing bar 3-4 and the longitudinal reinforcing bar 3-5 is waved.

The elastic pressure sensing diaphragm 3 is a circular chip, oval chip or chip with other geometrical shapes, with a thickness of between 0.1 mm and 2.0 mm. The elastic pressure sensing diaphragm 3 applied in this example is a circular chip, with a thickness of 0.5 mm.

The elastic pressure-sensing diaphragm 3 is made of rubber, silastic, thermoplastic elastomer (TPE) or other high elastic macromolecule material. In the example, rubber is employed.

An application method of the pressure indicator is summarized as follows.

Pressure measurement of a gas bag is taken as an example. As shown in FIG. 1, while the pressure indicator is in use, the lower mouth 5-3 is in airtight connection with the gas bag via an inflating tube. A syringe needle is applied to inflate the pressure indicator via the upper opening 1-1, and the gas enters the lower space 1-3 via the check valve 1-2, as shown in FIG. 2. Then, the gas passes through the gap 1-4 in FIG. 1 and enters the upper space 5-1 of the lower cover 5. On the one hand, as shown in FIG. 1, the gas passes through the holes 4-3 beneath the transmission indication rod 4, enters the lower space 5-2, and inflates the gas bag via the lower mouth 5-3. On the other hand, as shown in FIG. 1, the gas pushes the lower surface 3-3 of the elastic pressure-sensing diaphragm 3 to move upward, and pushes upward the transmission indication rod 4 in the same time, so that the change of the indication end 4-4 indicates the pressure change and that the number is accessible on the calibration line outside the lower cover. The upper surface of the elastic pressure-sensing diaphragm 3 communicates with the air via the air channel 1-5. The elastic pressure-sensing diaphragm 3 always indicates the pressure difference between the gas bag and atmosphere, and the structure of the pressure indicator guarantees the accuracy of the measurement.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. A pressure indicator, comprising:
a) a check valve;
b) an upper cover, the upper cover comprising an inner wall, a circular groove, and a positioning bulge;
c) an intermediate member, the intermediate member comprising a positioning groove and a lower port;
d) an elastic pressure-sensing diaphragm, the elastic pressure-sensing diaphragm comprising a circumferential flange and a lower surface;
e) a transmission indication rod, the transmission indication rod comprising a support end, a connection rod, and an indication end; and
f) a lower cover;
wherein:
the check valve is disposed in the upper cover, and the inner wall of the upper cover and the check valve are assembled to form an upper opening;
the circular groove is disposed on a shoulder of the upper cover;
an opening of an air channel which communicates with ambient air is disposed inside the circular groove;
the positioning bulge of the upper cover is connected to the positioning groove of the intermediate member;
the lower port of the intermediate member is fixedly connected to the circumferential flange of the elastic pressure-sensing diaphragm;
the lower surface of the elastic pressure-sensing diaphragm is provided with a groove configured to coordinate with the support end of the transmission indication rod;
the connection rod is connected to a top and bottom of the support end, and the indication end comprises holes on two sides thereof;
at least one surface of the elastic pressure-sensing diaphragm is provided with at least one circular or oval circumferential reinforcing bar and at least one longitudinal reinforcing bar which diffuses from center to all round;
the longitudinal reinforcing bar is between 2 and 16 in number;
the longitudinal reinforcing bar and the circumferential reinforcing bar are uniformly distributed in a vertically crossing way; and
a cross section of the circumferential reinforcing bar and the longitudinal reinforcing bar is designed to be waved, rectangular, or triangular.
2. The pressure indicator of claim 1, wherein the air channel is formed by and runs through the upper cover and the intermediate member.

3. The pressure indicator of claim 1, wherein the elastic pressure-sensing diaphragm is a circular piece or an oval piece, with a thickness thereof of between 0.1 mm and 2.0 mm.

4. The pressure indicator of claim 1, wherein the elastic pressure-sensing diaphragm is made of rubber, silastic, or thermoplastic elastomer (TPE).

\* \* \* \* \*